(12) United States Patent
Koop et al.

(10) Patent No.: US 6,451,007 B1
(45) Date of Patent: Sep. 17, 2002

(54) THERMAL QUENCHING OF TISSUE

(76) Inventors: Dale E. Koop, 746 Southview Way, Woodside, CA (US) 94062; Jonathan M. Baumgardner, 11802 Kemper Rd., Auburn, CA (US) 95603; Robert A. Weiss, 54 Scott Adam Rd., Hunt Valley, MD (US) 21030

(*) Notice: Subject to any disclaimer, the term of this patent is extended or adjusted under 35 U.S.C. 154(b) by 0 days.

(21) Appl. No.: 09/364,275

(22) Filed: Jul. 29, 1999

(51) Int. Cl.$^7$ .............................................. A61B 18/18
(52) U.S. Cl. .............................. 606/9; 606/20; 606/22; 606/7; 128/898
(58) Field of Search ........................... 607/88, 89–94; 606/9, 8, 10–13, 20–24; 128/898

(56) References Cited

U.S. PATENT DOCUMENTS

| | | | |
|---|---|---|---|
| 3,630,203 A | 12/1971 | Sellinger et al. | 128/303.1 |
| 4,020,383 A | 4/1977 | Labadini et al. | |
| 4,376,376 A | 3/1983 | Gregory | 62/51 |
| 4,860,744 A | 8/1989 | Johnson et al. | 128/303 |
| 5,020,995 A | 6/1991 | Levy | 433/215 |
| 5,057,104 A | 10/1991 | Chess | 606/9 |
| 5,098,428 A | 3/1992 | Sandlin et al. | 606/22 |
| 5,207,670 A * | 5/1993 | Sinofsky | 606/8 |
| 5,337,741 A | 8/1994 | Diamond | |
| 5,344,418 A | 9/1994 | Ghaffari | 606/9 |
| 5,409,479 A * | 4/1995 | Dew et al. | 606/9 |
| 5,624,435 A * | 4/1997 | Furumoto et al. | 606/10 |
| 5,725,522 A * | 3/1998 | Sinofsky | 606/8 |
| 5,746,735 A * | 5/1998 | Furumoto et al. | 606/9 |
| 5,746,736 A * | 5/1998 | Tankovich | 606/9 |
| 5,814,040 A * | 9/1998 | Nelson et al. | 606/9 |
| 5,820,626 A | 10/1998 | Baumgardner | 606/13 |
| 5,885,274 A * | 3/1999 | Fullmer et al. | 606/9 |
| 5,928,222 A * | 7/1999 | Kleinerman | 606/16 |
| 5,968,034 A * | 10/1999 | Fullmer et al. | 606/9 |
| 5,979,454 A * | 11/1999 | Anvari et al. | 128/898 |
| 6,059,820 A * | 5/2000 | Baronov | 607/89 |
| 6,171,301 B1 | 1/2001 | Nelson et al. | |
| 6,248,103 B1 | 6/2001 | Tannenbaum et al. | |

FOREIGN PATENT DOCUMENTS

| | | |
|---|---|---|
| DE | 195 12 481 A1 | 4/1994 |
| EP | 0 736 308 A2 | 9/1996 |
| EP | 0 736 308 A3 | 6/1998 |
| WO | WO 01/08545 A | 2/2001 |

OTHER PUBLICATIONS

Spatially selective photocoagulation of biological tissues: feasibiliy study utilizing cryogen spray cooling, Applied Optics; vol. 35, No. 19; Anvarie et al., Jul. 1, 1996, 9 pages.

Selective cooling of biological tissues: application for thermally mediated therapeutic procedures, Anvari et al., Phys. Med. Biol. 40 (1995) 241–252.

Handpiece Extender brochure, Spectrum Medical Technologies, Inc., RD 1100, RD 1200, 2 pages.

Anvari et al., Spatially Selective Photocoagulation of Biological Tissues: A Feasibility Study Utilizing Cryogen Spray Cooling. *App. Optics,* in press as of Jan. 8, 1996.

Omega Micro Infrared Temperature Transducer OS40 Series. Omega Complete Temperature Measurement Handbook and Encyclopedia (a registered trademark), vol. 28, pages cover, J–45 and J–46 (1992).

* cited by examiner

*Primary Examiner*—Linda C. M. Dvorak
*Assistant Examiner*—Ahmed Farah
(74) *Attorney, Agent, or Firm*—Ray K. Shahani, Esq.; Robert D. Fish, Esq.

(57) ABSTRACT

A method for selective heating of subsurface structures in material such as tissue includes a cooling device for thermally quenching or removing heat from the top surface of tissue during or just after delivering pulsed energy to target or subsurface structures or tissue, a preferred embodiment of the invention using dynamic cooling, to quench the thermal energy conducted from the targeted structure into surrounding tissue.

21 Claims, 4 Drawing Sheets

THERMAL QUENCHING OF TISSUE

FIELD OF THE INVENTION

This invention is related delivery of laser or other source of thermal energy to biological or other tissue for treatment therein, and more particularly, to a method and system for delivery of the laser or other source of thermal energy to the target tissue wherein surrounding tissue, including surface tissue, is also elevated in temperature by conduction of heat from the target tissue, and wherein thermal quenching of the surrounding tissue, and in particular the surface tissue, prevents thermal damage thereto.

BACKGROUND OF THE INVENTION

It is sometimes desirable to cause heat affected changes in a selected structure in tissue, such as a vein or hair follicle, without causing heat affected changes in tissue adjacent to the selected structure. The prior art treatments use a method called selective photothermalysis, whereby laser or pulsed light source is tuned to a wavelength whereby its energy is preferentially absorbed by a preselected target. The energy from the source is delivered within a time period short enough for heat to build up in the target and faster than it flows into adjacent regions by thermal conduction. The amount of energy or fluence delivered to the target is chosen such that the temperature rise in the targeted region results in an intended thermal treatment of the target.

Vascular lesions have been treated for more than twenty years with a variety of lasers and light sources including pulsed dye lasers, argon lasers, Nd:YAG lasers, and flashlamps. The pulsed dye laser operating at a wavelength of 577 nanometers is very effective since it can penetrate through skin and is S absorbed by hemoglobin in smell veins resulting in heat build up and a photo-coagulation of the vein. The energy is confined to a short time period, less than the thermal relaxation time of the vessel being treated, so that heat loss to surrounding tissue is minimized during treatment. The principal is known as, or at least has been characterized as, selective photothermalysis. *Selective Photothermalysis*, Anderson, R. R, Parrish, J. A., Science 1983 Vol 220 Pages 524–527

Although the pulsed dye laser is useful for many smaller vessels, in lesions such as port wine stains, the larger and deeper lying vessels found in leg telangiactasias and other undesirable lesions are difficult to treat. The pulsed dye laser energy is absorbed too strongly by hemogolobin and so does not penetrate fully though larger veins which approach diameters of 0.1 mm to 3 mm in diameter. Larger vessels also require more energy to achieve the same coagulative effect and have longer thermal relaxation times. A variety of lasers and a non-coherent intense light source with tunable wavelength have all been used to treat vessels of different sizes and depths in skin.

Melanin absorption of laser energy results in some heating of the epidermis by each of the various energy sources used for vascular treatment. Several methods have been described for cooling the surface of skin during treatment to minimize the risk of thermal injury to tissue adjacent to the targeted veins. One early method included pre-cooling with ice for several minute prior to treatment.

U.S. Pat. No. 5,282,797 issued Feb. 1, 1994 to Chess describes a method of circulating cooling fluid over a transparent plate in contact with the treatment area to cool the epidermis during treatment.

U.S. Pat. No. 5,344,418 issued Sep. 6, 1994 to Ghaffari describes a method whereby a coolant is used for a predetermined time interval in coordination with the delivery of laser energy to optimize the cooling of the epidermis and minimize cooling of the targeted vessel.

U.S. Pat. No. 5,814,040 issued Sep. 29, 1998 to Nelson et al. describes a dynamic cooling method whereby a cryogenic spurt is applied for a predetermined short time directly onto the skin in the target region. The time period is well controlled and limited so that cooling is confined only to the epidermis while leaving the temperature of deeper port wine stains substantially unchanged.

The result of the various cooling methods is that a greater fluence can be used to treat vessels without significant thermal damage during treatment to the epidermis. Avoiding epidermal damage is extremely important for the treatment of deeper and larger vessels since the fluences and wavelengths used could cause substantial damage to uncooled epidermis.

Problems associated with the prior art include the subsequent conduction of heat away from the treated vessels or other target tissue into adjacent tissue. For larger vessels, a significant amount of heat builds up during the treatment. The treated vessels cool off by thermal conduction to surrounding tissue. The temperature of the tissue adjacent to the vessel will rise immediately after treatment and may reach levels causing significant patient discomfort and even epidermal damage.

Therefore what is needed is a method and device which subsequently cools and quenches heat build up in tissue, and especially in surface tissue, adjacent to tissue or structures treated in the thermally-mediated process or treatment.

ADVANTAGES AND SUMMARY OF THE INVENTION

It is therefore an advantage and an object of the present invention to provide an improved system for selectively cooling tissue during photothermal treatment.

It is a further advantage of the present invention to provide such a system which uses dynamic cooling to quench heat build up during and after photothermal treatment.

It is a further advantage of the present invention to provide such a system which selectively heats a subsurface structure in tissue and subsequently quenches heat build up in non-target tissue.

It is a further advantage of the present invention to reduce the level of pulsed energy needed for treatment by minimizing precooling of the tissue.

It is a further advantage of the present invention to provide such a system which selectively heats a subsurface structure in skin to cause thermal affected changes in said subsurface structure without significant epithelial damage due to subsequent heating from the target region.

It is a further advantage of the present invention to provide such a system which selectively heats vascular lesions in tissue and quenches subsequent heat build up in epithelial tissue.

It is a further advantage of the present invention to provide such a system which selectively heats hair follicles in tissue and quenches subsequent heat build up in epithelial tissue.

It is a further advantage of the present invention to require less cooling of the target area than is typically required, resulting in more efficient heating of the selected target and less thermal damage to surrounding tissue.

In a preferred embodiment, the system for generating light energy is a laser system such as but not limited to a solid-state laser, including but not limited to a neodymium-doped yttrium-aluminum-garnet (Nd:YAG) laser.

In additional preferred embodiments, the system for generating light energy is a gas discharge flashlamps or an incandescent-type filament lamp.

The energy from the generating system may be directed into or coupled to a delivery device such as but not limited to a fiber optic or articulated arm for transmitting the light energy to the target tissue.

The light energy may be focused on tissue with a focusing lens or system of lenses.

The surface of the tissue may be cooled with a cooling device including but not limited to an irrigating solution, a spray or flow of refrigerant or other cryogenic material, or a transparent window cooled by other active means, or other dynamic or passive cooling means.

The tissue may be preheated with a heating device such as, but not limited to an intense light source, a flashlamp, a filament lamp, laser diode, other laser source, electrical current, or other electromagnetic or mechanical energy which penetrates into layers of tissue beneath the surface. The preheating can occur simultaneously or just prior to the surface cooling of tissue from the cooling device such that the tissue preheating results in a temperature rise in underlying layers of tissue, and a temperature profile results. The pulsed application of energy from the energy delivery device results in a temperature profile that preferentially heats a selected structure or target in tissue, and the post cooling prevents thermal damage to tissue adjacent to that structure. This also reduces the overall pulse energy level needed of the pulsed treatment device due to the fact that a desirable temperature profile exists prior to delivery of the pulsed treatment energy.

The tissue may be post cooled with a dynamic cooling device such as, but not limited to a pulse, spray or other flow of refrigerant such that the post cooling occurs after a temperature rise in an underlying targeted structure and a temperature profile results such that the pulsed application of energy from the energy delivery device results in a temperature profile that preferential heats a selected structure in tissue without subsequent undesirable heating to tissue adjacent to that structure from thermal conduction.

Numerous other advantages and features of the present invention will become readily apparent from the following detailed description of the invention and the embodiments thereof from the claims and from the accompanying drawings.

DETAILED DESCRIPTION OF THE PREFERRED EMBODIMENT

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

Figure 1:
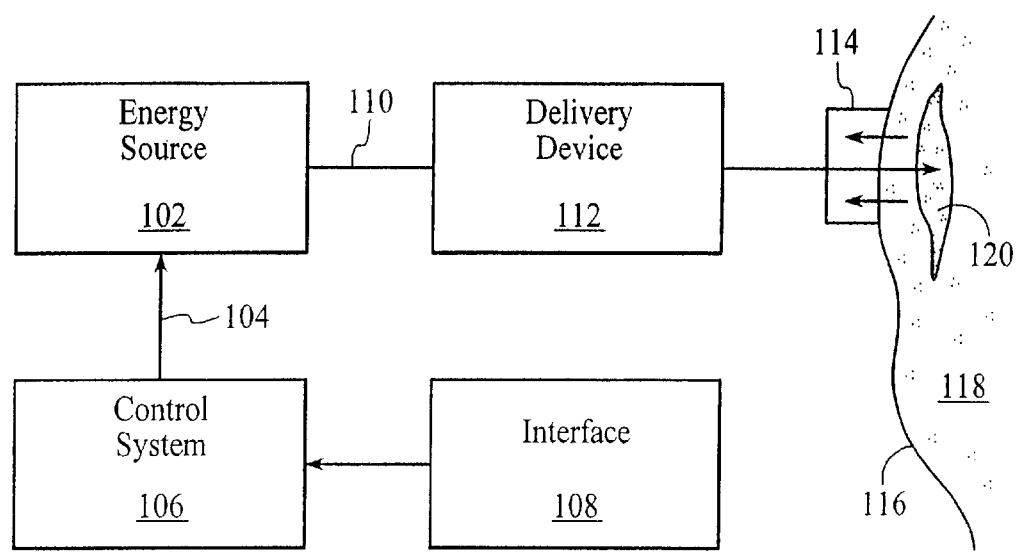
FIG. 1 is a representative schematic block diagram of a preferred embodiment of a system for thermal quenching of tissue of the present invention.

FIG. 1 is a representative schematic block diagram of a preferred embodiment of a system 100 for thermal quenching of tissue of the present invention. Operation of energy source 102 to produce energy for delivery by the system 100 is controlled according to control signal 104 from control system 106. Control system 106 includes a physician interface 108 for operating the system. Said interface 108 optionally includes a footswitch for energy delivery, display and interactive and/or menu driven operation utilizing operator input, prompts, etc. Additional energy delivery control interface means shall be known to those skilled in the art.

In a preferred embodiment, energy source 102 is a neodymium doped yttrium-aluminum-garnet (Nd:YAG) laser, energized by a flash-lamp or laser diode. Energy source 102 is controlled by control system 106 which comprises the (software and electronics to monitor and control the laser system, and interface 108. The beam of laser energy 110 from the energy source 102 is directed into a delivery device 112 which may be an optical fiber, a fiber bundle or articulated arm, etc.

Modem instruments to provide dynamic cooling of the surface layers of tissue or other materials are well suited to these applications. A coolant spray can be provided through a handpiece or it could be provided with another separate device. Finally, a connection to a computer and the control system 106 of the energy source 102 will allow the system 100 to utilize electronic or other thermal sensing means and obtain feedback control signals for the handpiece. An optimum cooling strategy might be one that uses a post-irradiation cooling spurt that provides cooling or dissipation of the epidermal heat generated by absorption of energy in the non-isotropic skin, optionally containing various pigmentation levels. An appropriate cryogen spray would be liquid nitrogen or tetrafluoroethane, $C_2H_2F_4$, an environmentally compatible, non-toxic, non-flammable freon substitute. In clinical application the distance between the aperture of the spray valve and the skin surface should be maintained at about 20 millimeters.

In a preferred embodiment of the present invention, upon delivery of laser energy onto the surface and therethrough, the target tissue will be raised to the optimal treatment temperature and generally not any higher, in an adequately rapid process, with the surface temperature of the skin remaining at a temperature below the threshold for damage temperature. It will be understood that the threshold for damage temperature is the temperature below which the skin or other tissue can be elevated without causing temporary or permanent thermal damage, and above which the tissue may undergo either transient or long term thermally induced physiological change. As described, the wavelength of irradiated light energy is selectively absorbed by hemoglobin or hair follicles, or other tissue with pigmentation or chromophores of a certain type, but passes through the surface and overlying/adjacent tissue to the target tissue with minimal absorption. However, once the target tissue or structure becomes elevated in temperature, surrounding and adjacent tissue will become hot due to conduction of heat from the target tissue or structures. Post-irradiation cooling can then be initiated, and tissue other than the target tissue is prevented from increasing in temperature beyond the threshold of damage or adverse effect. Adverse effects of elevated tissue surface temperature include discomfort or pain, thermal denaturing of proteins and necrosis of individual cells at the surface only, or deeper tissue ablation potentially leading to hyperplasia, scarring, or hyperpigmentation, a proliferation of cells formed in response to the induced trauma. In a preferred embodiment of the method of the present invention, heating and subsequent post-cooling are performed in a predetermined timing sequence, optionally with the use of timer circuits and/or other controller means.

Thus, it will be obvious; to those skilled in the art that a passive heat sink includes glass or sapphire tip probes, and other types of devices to lay on the surface of the skin. It will also be obvious that a dynamic type of heat sink will refer to those actively cooled by flowing gas or liquid, jets or spurts of coolant such as freon, and other active types of heat exchangers suitable for surface cooling while irradiating sub-surface portions of collagen tissue. U.S. Pat. No. 5,820,626 issued Oct. 13, 1998 to Baumgardner and U.S. application Ser. No. 08/938,923 filed Sep. 26, 1997 by Baumgardner et al., both incorporated herein by reference in their entireties, teach a cooling laser handpiece with refillable coolant reservoir, and can be utilized as a handpiece for delivery device 112 and heat sink 114.

Figure 2:
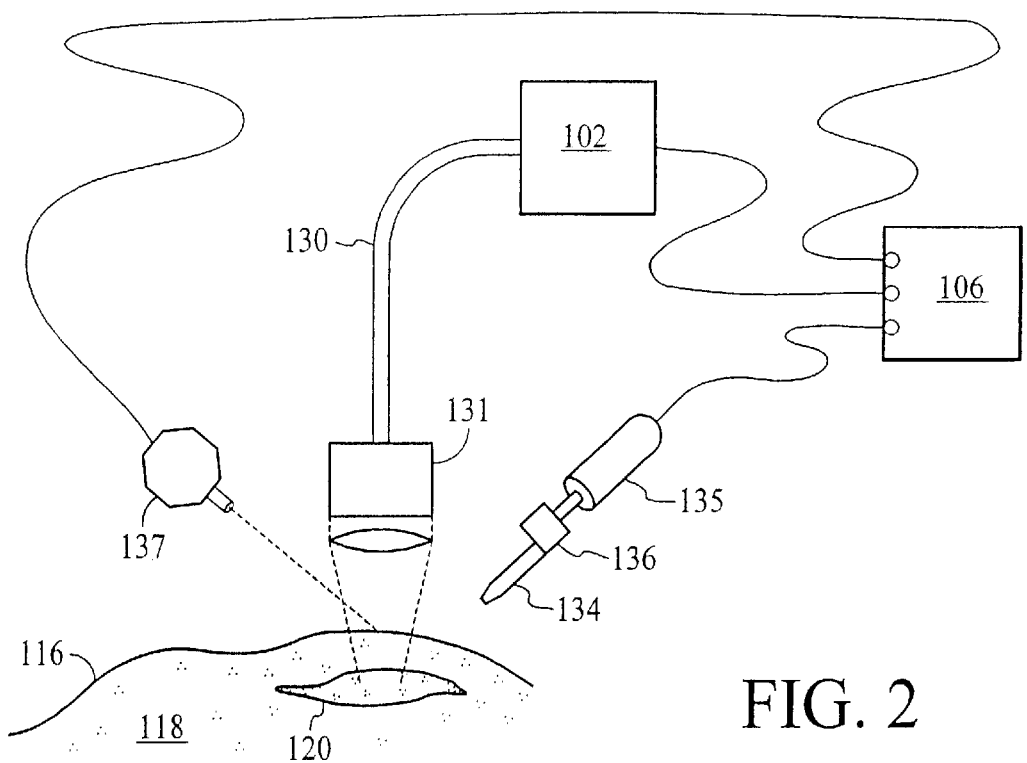
FIG. 2 is a more detailed representative schematic block diagram of a preferred embodiment of the delivery device shown in FIG. 1 of the present invention.

FIG. 2 is a more detailed representative schematic block diagram of a preferred embodiment of the delivery device 112 shown in FIG. 1 of the present invention. The energy from the energy source 102 is directed into delivery device 112 via a delivery channel 130 which may be a fiber optic, articulated arm, or an electrical cable etc. At the distal end of delivery device 112 is a energy directing means 131 for directing the pulsed energy toward the surface tissue 116 and overlaying tissue 118 overlaying the target tissue or structure 120. A nozzle 134 is useful for directing coolant from reservoir 135 to the tissue 118, and a valve 136 for controlling the coolant interval. A temperature sensor 137 may be used to monitor the temperature rise of the target tissue 118. Control system 106 monitors the temperature signal from sensor 137 and controls valve 136 and energy source 102. Reservoir 135 may be in the delivery device 112 or elsewhere, and contains a refrigerant which may be applied to surface tissue 120 by spraying said refrigerant from cooling nozzle 124 in conjunction with delivery of pulsed treatment energy to the patient.

Figure 3:
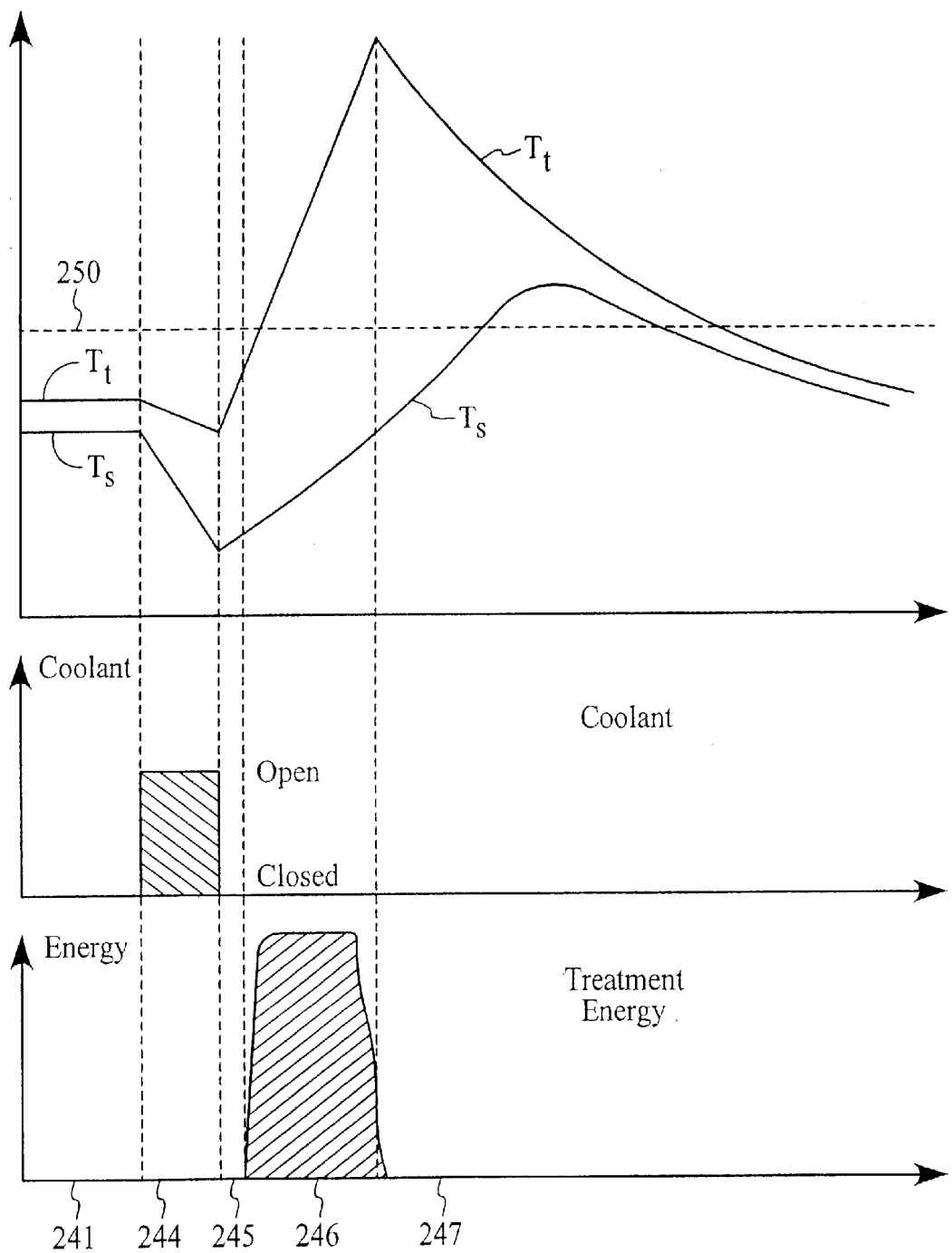
FIG. 3 is a representative sample data plot of the temperature of surface tissue and target tissue achieved by methods and systems of the prior art having precooling.

FIG. 3 is a representative sample data plot of the temperature of surface tissue 116 and target tissue 120 achieved by methods and systems of the prior art having precooling. The waveforms are representative of oscilloscope-type traces which reproduce signals generated by one or more thermal detectors. In general, with precooling the coolant is applied just prior to the delivery to the pulsed energy. Waveform 240 indicates the periods of time and associated temperatures of the target tissue and the surface tissue during the processes of the prior art. Initially, as indicated by time period 241, the temperature of the surface tissue 116 as well as the target tissue 120, as shown in FIGS. 1 and 2, are at $T_s$ and $T_t$ respectively. It will be understood that typically the skin surface is at a temperature somewhat below actual body temperature. Typically, this range might be between about 28 and about 34 degrees Celsius. Furthermore, a target vein, hair follicle or other structure can be assumed to be at about or somewhat just below 37 degrees Celsius, or actual body temperature. Once the refrigerant is applied to surface tissue 116 by opening valve 136 during a subsequent time period 244, the temperature $T_s$ drops to a level determined by the length of time 244 for which the surface tissue 120 is exposed to the coolant. By way of example, for time periods of about 30 milliseconds, $T_s$ may drop from a typical temperature of about 32 degrees Celsius to just above 0 degrees Celsius. However, as the target tissues 120 is deeper than the surface 116, initially $T_t$ is not significantly affected and may drop by only a few degrees. A short delay 245 following delivery of refrigerant may be used, and is typically between 0 and 100 milliseconds. This allows time for cooling of at least a layer of epidermis to a depth of 50 to 250 micrometers. Following time periods 244 and optional period 245, the pulsed energy is applied over predetermined or other time period 246. The time period 246 depends on the size of the target and the fluence delivered, as indicated by principles of selective photothermalysis. For example. in experiments with an Nd:YAG laser operating at 1064 nanometers, one application of a 10 millisecond period and a fluence of 50 joules per square centimeter was sufficient to treat small blood vessels, and fluences of up to 150 joules per square centimeter and time periods of up to 200 milliseconds are useful for treating larger vessels of 1 to 3 millimeters in cross-section. During period 246 $T_t$ increases to a therapeutically effective value, whereas $T_s$ remains below the threshold indicated as 250 for patient discomfort or tissue damage.

Subsequent to treatment, the target tissue 116 cools by conduction of thermal energy to adjacent overlaying tissue 118 including the surface tissue 116, with a resultant temperature rise in the target tissue 120 dependant on the size and depth of the target tissue 120. As $T_t$ equalizes with surrounding tissue, the $T_s$ may rise above the level of patient discomfort and even cause damage to surface tissue 116.

FIG. 3 is a representative sample data plot of the temperature of surface tissue 116 and target tissue 120 achieved by methods and systems of the prior art having precooling.

Figure 4:
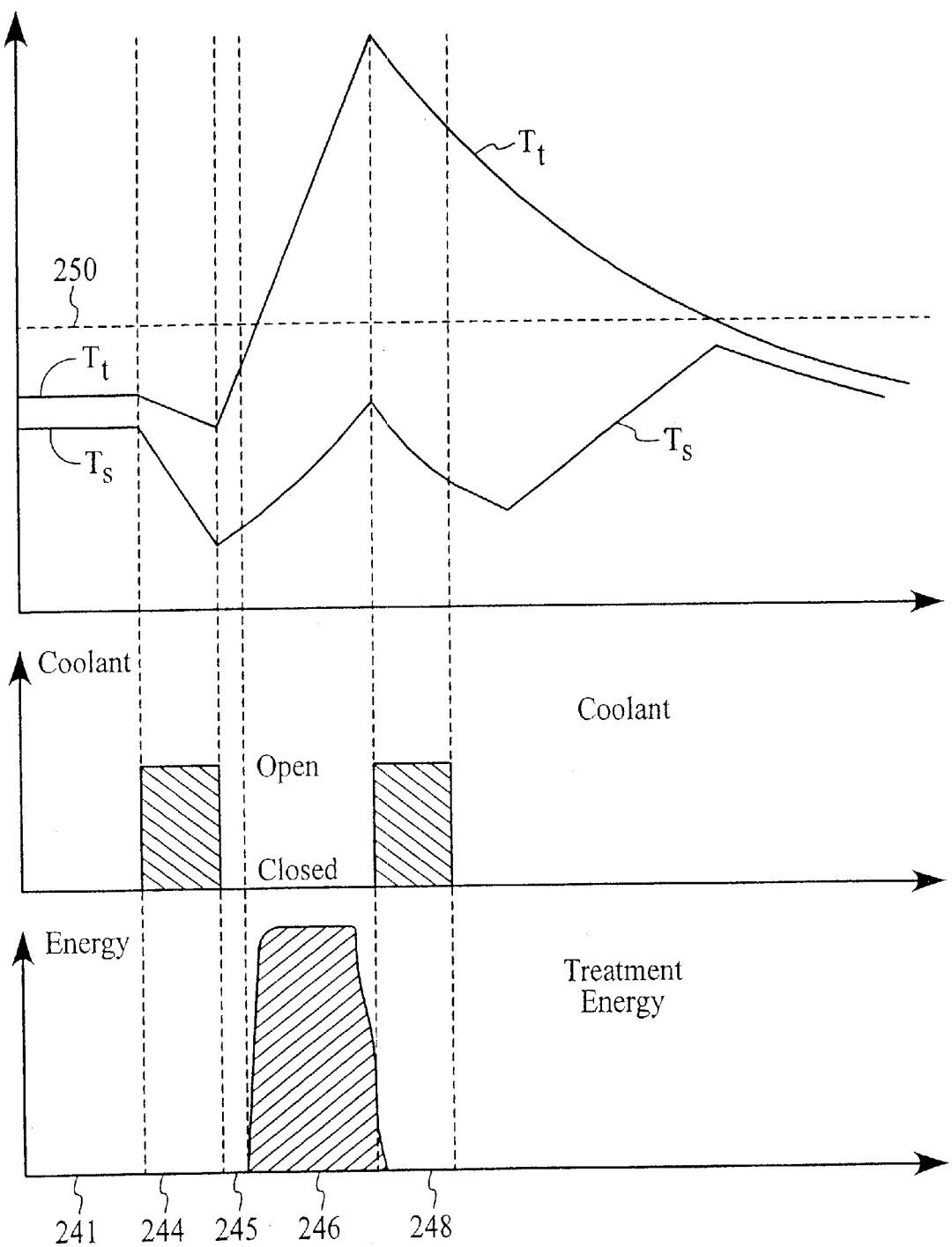
FIG. 4 is a representative sample data plot of the temperature of surface tissue and target tissue achieved by a preferred embodiment of the method and system of the present invention such as shown in FIGS. 1 and 2 having precooling.

FIG. 4 is a representative sample data plot of the temperature of surface tissue 116 and target tissue 120 achieved by a preferred embodiment of the method and system of the present invention such as shown in FIGS. 1 and 2 having precooling. The method of the present invention includes the process of precooling surface tissue 116 and target tissue 120 slightly, followed by a short time period 245 and subsequent delivery of thermal energy to the body during time period 246 such as shown in FIG. 3. In the present invention, however, refrigerant is also applied subsequent to the energy pulse by opening valve 136 as desired or as indicated, thus keeping $T_s$ below the threshold for damage temperature 250. FIG. 4 shows a pulse of coolant applied during time period 248 which is subsequent to the application of pulsed energy during period 246. This results in thermal quenching of the surface tissue 116. The thermal quenching pulse or other flow of refrigerant or other means for cooling is applied after the beginning of treatment period 246 and may be initiated before or after the end of time period 246. It is important that the peak or highest temperature of the surface tissue 116 never rise above the threshold for damage temperature 250. The time point at which the peak temperature in the surface tissue 116 is achieved is dependant on the size and depth of the target 120.

In one experimental example, cryogenic fluid was applied to the surface tissue 116 within 10 milliseconds of the end of the energy pulse of time period 246 and for a duration 248 of 20 milliseconds. For vascular treatment with an Nd:YAG laser with pulse widths of 5 milliseconds to 200 milliseconds, the period of thermal quenching 2413 preferably 10 milliseconds to 30 milliseconds immediately after the treatment energy. This sequence significantly reduced patient discomfort compared to treatment with out thermal quenching. The effect of thermal quenching is not dependant on pre-cooling and may be used as the only method of cooling in many cases.

Figure 5:
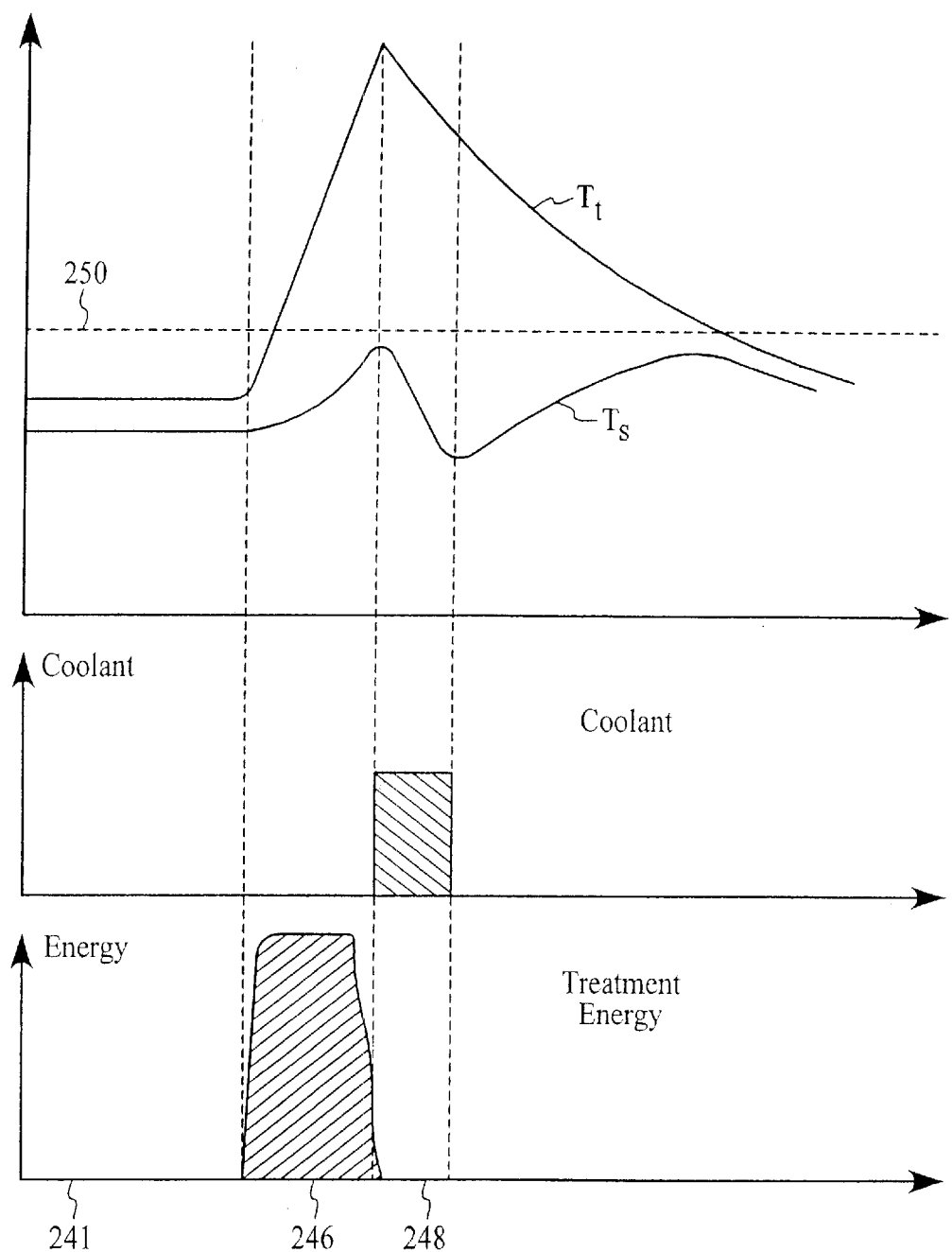
FIG. 5 is a representative sample data plot of the temperature of surface tissue and target tissue achieved by a preferred embodiment of the method and system of the present invention such as shown in FIGS. 1 and 2 without precooling.

FIG. 5 is a representative sample data plot of the temperature of surface tissue and target tissue achieved by a preferred embodiment of the method and system of the present invention such as shown in FIGS. 1 and 2 without precooling. As in the method shown in FIG. 4, the thermal quenching pulse or other flow of refrigerant or other means for cooling over time period 248 is applied after the beginning of treatment period 246 and may be initiated before or after the end of time period 246. It is important that the peak or highest temperature of the surface tissue 116 never rise above the threshold for damage temperature 250.

The present invention requires less cooling of the target tissue, structure or area during the treatment phase than is typically required, resulting in more efficient heating of the selected target and less thermal damage to surrounding tissue.

It will be understood that while numerous preferred embodiments of the present invention are presented herein, numerous of the individual elements and functional aspects of the embodiments are similar. Therefore, it will be understood that structural elements of the numerous apparatus disclosed herein having similar or identical function may have like reference numerals associated therewith.

In a preferred embodiment of the present invention, re-heating of tissue, especially target or subsurface tissue can be useful. U.S. application Ser. No. 09/185,490 filed Nov. 3, 1998 by Koop et al. teaches methods and systems for performing subsurface heating of material and in incorporated herein by reference in its entirety. In these methods, target or subsurface tissue is preheated to an elevated, non-destructive temperature which is somewhat below that of treatment. Thereafter, the temperature of the target tissue or structures is raised to treatment temperature. Once this second increase in temperature is achieved, the target tissue or structures will conduct heat into the body, especially to adjacent tissue and surface tissue, at which time the post-cooling of the present invention can be initiated so as to prevent damage to adjacent tissue or dermis or other surface tissue.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method for treatment of target tissue or structures with a source of pulsed electromagnetic energy with thermal quenching of adjacent or surface tissue, the method comprising the following steps:
   (A) Generating pulsed energy from an energy source;
   (B) Delivering the pulsed energy to the target tissue or structures with a delivery device;
   (C) Irradiating the target tissue or structures with the pulsed energy to cause selective thermally mediated treatment of the target tissue or structures such that there is minimal absorption of energy in surface tissue and adjacent tissue and selective absorption of energy in target tissue, and such that surface tissue remains at a temperature below the threshold for damage temperature during irradiation; and
   (D) Thermal quenching of tissue adjacent or overlying the treated target tissue with cooling times of about 30 milliseconds subsequent to step B with delay times between about 0 to about 15 milliseconds to prevent undesired temperature rise in adjacent or overlying tissue due to conduction of heat from the treated target tissue into the adjacent or overlying tissue.

2. The method of claim 1 in which the selective thermally mediated treatment of the target tissue or structures is for the treatment of vascular tissue.

3. The method of claim 1 in which the selective thermally mediated treatment of the target tissue or structures is for the treatment of tissue containing collagen.

4. The method of claim 1 in which the selective thermally mediated treatment of the target tissue or structures is for the treatment of cartilage.

5. The method of claim 1 in which the selective thermally mediated treatment of the target tissue or structures is for the treatment of tissue containing pigment.

6. The method of claim 1 in which the selective thermally mediated treatment of the target tissue or structures is for the hair removal treatment.

7. A method of thermal quenching of surface tissue during selective thermally mediated treatment of target tissue or structures, the method comprising the steps of: delivering energy to the target tissue or structures to increase the temperature of the target tissue or structures to a predetermined treatment temperature such that there is minimal absorption of energy in surface tissue or other tissue adjacent the target tissue, and selective absorption of energy in target tissue, and surface tissue remains at a temperature below the threshold for damage temperature during irradiation; and subsequently cooling the surface tissue or other tissue adjacent the target tissue or structures, with cooling times of about 30 milliseconds with delay timers between about 0 to about 15 milliseconds, to prevent undesired heating of the surface tissue or other tissue adjacent the target tissue due to conduction of heat from the treated target tissue into the adjacent or overlying tissue.

8. The method of claim 7 in which the step of cooling is initiated after elevation of the target tissue or structures to treatment temperature.

9. The method of claim 7 in which the step of cooling is initiated prior to elevation of the target tissue or structures to treatment temperature.

10. The method of claim 7 in which the step of cooling is initiated concurrently with elevation of the target tissue or structures to treatment temperature.

11. The method of claim 7 in which the step of cooling is initiated subsequent to an increase in the temperature of the surface tissue or other tissue adjacent the target tissue or structures.

12. The method of claim 7 in which the energy is pulsed and delivered at a rate of between about 50 Joules per square centimeter and about 150 Joules per square centimeter.

13. The method of claim 7 in which the energy has a pulse width of between about 5 milliseconds and about 200 milliseconds.

14. The method of claim 7 in which the step of cooling includes delivery of refrigerant to the surface tissue for a period of between about 10 milliseconds and about 30 milliseconds.

15. The method of claim 7 in which the step of cooling the surface tissue or other tissue adjacent the target tissue or structures is performed using passive cooling means.

16. The method of claim 7 in which the target tissue or structures is veins and in which the treatment is vascular treatment.

17. The method of claim 7 in which the target tissue or structures is hair follicles and in which the treatment is hair removal.

18. The method of claim 7 in which the step of cooling the surface tissue or other tissue adjacent the target tissue or structures is performed using dynamic cooling means.

19. The method of claim 18 in which the dynamic cooling means cools the surface tissue or other tissue adjacent the target tissue or structures by delivering a liquid refrigerant to the surface tissue or other tissue adjacent the target tissue or structures.

20. The method of claim 19 in which the liquid refrigerant is delivered to the surface tissue or other tissue adjacent the target tissue or structures for a period of time between about 10 milliseconds and about 30 milliseconds.

21. The method of claim 19 in which the target tissue or structures is tissue containing pigmentation and in which the treatment is modification of the pigmentation.

* * * * *